United States Patent [19]

Okuda et al.

[11] Patent Number: 4,830,616

[45] Date of Patent: May 16, 1989

[54] METHOD FOR BONDING COMPOSITE RESIN TO DENTIN

[75] Inventors: Reiichi Okuda, No. 8-27-8, Nakayama, Sendai-shi, Miyagi-ken; Masashi Komatsu; Shin Asanuma; Noriko Hiratsuka, all of Sendai, Japan

[73] Assignees: Reiichi Okuda, Sendai; G-C Dental Industrial Corp., Tokyo, both of Japan

[21] Appl. No.: 183,097

[22] Filed: Apr. 19, 1988

[30] Foreign Application Priority Data

May 21, 1987 [JP] Japan .................. 62-122658

[51] Int. Cl.$^4$ .............................................. A61C 5/00
[52] U.S. Cl. ................... 433/217.1; 433/226; 433/228.1; 523/116; 524/273
[58] Field of Search ................ 523/116; 524/273; 433/215-228.1

[56] References Cited

U.S. PATENT DOCUMENTS

| | | | |
|---|---|---|---|
| 4,259,075 | 3/1981 | Yamauchi et al. | 433/217.1 |
| 4,612,384 | 9/1986 | Omura et al. | 523/116 X |
| 4,654,007 | 3/1987 | Sigler et al. | 433/226 |
| 4,655,712 | 4/1987 | Croll | 433/229 |
| 4,748,198 | 5/1988 | Takahashi et al. | 524/273 |

OTHER PUBLICATIONS

Search Report for British Application No. 8809801.7, 10/25/88.

*Primary Examiner*—Nancy Swisher
*Attorney, Agent, or Firm*—Oblon, Fisher, Spivak, McClelland & Maier

[57] ABSTRACT

A method for bonding a restorative composite resin to dentin which comprises:

treating the surface of dentin with a dentin-treating liquid for, 1 to 90 seconds obtained by adding glutaraldehyde and ferric chloride to an aqueous solution of ethylenediaminetetraacetic acid regulated to a hydrogen ion concentration (pH) of 7.4; removing the treating liquid by water-rinsing to dry the thus treated surface of dentin; applying a primer comprising an ethylene related unsaturated monomer, a (meth)acrylic ester polymer and tri-n-butyl borane on the dried surface of dentin; and filling the restorative composite resin onto the applied surface of dentin.

8 Claims, No Drawings

METHOD FOR BONDING COMPOSITE RESIN TO DENTIN

BACKGROUND OF THE INVENTION

1. Field of the Invention

The present invention relates to a bonding method having its object to improve the adhesion of a restorative composite resin to tooth substance, especially dentin in dental (conservation and restoration) conservative and restorative applications.

2. Statement of the Prior Art

As regards the methods for bonding a restorative composite resin to dentin, it has heretofore been confirmed that the clinically required bonding strength on the order of 150 kgf/cm$^2$ or higher is obtained therebetween by treating the enamel by acid etching with phosphoric acid or citric acid, followed by water rinsing and drying, and coating it with a primer which comprises of a methacrylic ester monomer and a curing agent and show no adhesion to dentin. For the bonding of the composite resin to dentin, however, a variety of dentin treating solutions or primers considered to be adhesive have been proposed, since the use of adhesion-free primers has resulted in poor adhesion. Japanese Patent Publication No. 55-30768 discloses phosphric ester compounds which are said to possess adhesion. Even with such compounds, however, satisfactory adhesion is not obtained, as noted from the fact that the resulting adhesive strength is as small as 90 kgf/cm$^2$ or less. Japanese Patent Laid-Open No. 54-12338 discloses 4-methacryloxyethyl trimellitic anhydride (4META) as a functional monomer. In a publication "Journal of the Japan Society for Dental Apparatus and Materials" 23(61), 29–32, 1982, it has been reported that an adhesive strength of 12 to 18 MPa is obtained by the restorative method wherein dentin is treated with an aqueous solution of 10% citric acid and 3% ferric chloride, and filled with a restorative material (4META-containing methyl methacrylate-tri-n-butyl borane/polymethyl methacrylate). However, such high adhesive strength could not be obtained by inventors' measuring method. Furthermore, a problem with the use of a chemical polymerization (chemically cured) type restorative composite resin comprising a redox catalyst system of tertiary amine/benzoyl peroxide (BPO) is that adhesion drops due to the reaction between tertiary amine and 4META.

Japanese Patent Laid-Open No. 60-172915 discloses a bonding method wherein dentin is treated with an aqueous solution of EDTA and, after water-rinsing and drying, is bonded with a primer comprising glutaraldehyde and hydroxyethyl methacrylate (HEMA). However, not only is this method time consuming due to the need of separate treatments, but also results in poor adhesive strength.

In view of the fact that not until now is any clinically satisfactory dentin-bonding method established, the present inventors have made studies of dentin-treating solutions and adhesive primers for the purpose of realizing a bonding method which can protect dental pulp while improving the adhesion to dentin in combination with its augmentation, and is applicable to the restorative composite resins of both chemical and light polymerization types. Thus, we have completed the present invention.

SUMMARY OF THE INVENTION

The present invention relates to a method for bonding dentin to a composite resin, which has its object to eliminate the aforesaid problems of the previous treatment. More specifically, according to the bonding method of the present invention, the surface of dentin to be bonded, from which decayed portions caused by caries attack have been removed, is treated for 1 to 90 seconds with a dentin-treating solution serving to remove smear layer present on that surface and, at the same time, fix and augment collagen on that surface, said liquid being an aqueous solution of EDTA, glutaraldehyde and ferric chloride, then said treating liquid is removed by water-rinsing, and the thus treated surface is dried by air-blowing. Then, a single thin layer of a primer that is a blend of a tri-n-butyl borane containing ethylene related unsaturated monomer with a (meth)acrylic ester polymer is applied on the dentin to be bonded, and a chemical polymerization type restorative composite resin comprising a redox catalyst system of tertiary amine/BPO or a light polymerization type restorative composite resin is filled thereon.

DETAILED EXPLANATION OF THE INVENTION

The present invention will now be explained in detail.

The dentin-treating solution used for the bonding method according to the present invention refers to an aqueous solution containing as the essential components three compounds, i.e., glutaraldehyde, ferric chloride and EDTA or its supernatant liquid, said aqueous solution being prepared by adjusting the hydrogen ion concentration (pH) of an aqueous solution of EDTA to 7.4 with a basic compound (it is noted, however, that although pH is variable in a range of 7.4±0.5 during adjustment, no practical problem arises) and, thereafter, adding thereto glutaraldehyde and ferric chloride. The concentration ranges of such three essential compounds are determined as follows.

The concentration of EDTA is usable in a range of 0.1 to 1.0 mol/l, preferably 0.3 to 0.5 mol/l. In concentrations below 0.1 mol/l, the capability of EDTA to remove smear layer is decreased, while in concentrations exceeding 1.0 mol/l, no further effect upon improvements in adhesion is expected, since insoluble matters are observed even by heating. The concentration of glutaraldehyde is usable in a range of 0.01 to 20 parts by weight, preferably 1 to 10 parts by weight with respect to 100 parts by weight of water. In concentrations below 0.01 part by weight, the incorporation of glutaraldehyde makes no or little contribution to an increase in adhesive strength, whereas 20 parts by weight or more of glutaraldehyde is undesirable from the stand point of pulp protection. The concentration of ferric chloride is usable in a range of 0.01 to 5.00 parts by weight, preferably 0.1 to 5.0 parts by weight with respect to 100 parts by weight of water. A certain degree of adhesive strength can be obtained without addition of ferric chloride, however, in concentrations below 0.01 part by weight, adhesive strength becomes unstable, while in concentrations exceeding 5.00 parts by weight, considerable insoluble matters remain so that no improvement in adhesive strength is observed.

Preferably, ethylene related unsaturated monomer incorporated into the primer used in the present method is a (meth)acrylic ester monomer which, by way of example, includes methyl methacrylate, ethyl methacrylate, ethylene glycol dimethacrylate, triethylene glycol dimethacrylate, tetraethylene glycol dimethacrylate, 1.4-butanediol dimethacrylate, neopentyl glycol dimethacrylate, trimethylolpropane trimethacrylate, 2,2-bis(4-methacryloxyphenyl)propane, 2,2-bis(4-methacryloxypolyethoxy)phenylpropane, 2-hydroxyethyl methacrylate, 3-hydroxyproply methacrylate and 1,3-bis(methacryloxyethoxy)benzene and others. Of these monomers which may be used alone or in combination, preference is given to a monomer composition containing methyl methacrylate as the main component, when taking the manipulation properties and adhesion to the primer into account.

By way of example, the (meth)acrylic ester polymer incorporated in the primer includes homopolymers obtained by the polymerization of monofunctional methacrylic ester monomers such as methyl methacrylate, ethyl methacrylate and n-butyl methacrylate or copolymers obtained by the copolymerization of two or more of such monomers. Of these homopolymers and copolymers which may be used alone or in combination, preference is given to the homopolymer of methyl methacrylate and/or the copolymer of methyl methacrylate with ethyl methacrylate.

Tri-n-butyl borane (TBB) incorporated separately as the activator in the primer may be used alone but, due to its instability in air, should preferably be diluted with an organic solvent such as ethyl ether or tetrahydrofuran or a plasticizer such as dioctyl phthalate, dibutyl sebacate or silicone oil for use. Use may also be made of TBB-(o) formed by partial oxidation of TBB. The amount of TBB, calculated as such, may be in the range of 0.2 to 10 parts by weight, but should preferably be in the range of 2 to 4 parts by weight with respect to 100 parts by weight of ethylene related unsaturated monomer, when curing properties and adhesion in mind.

EXAMPLES

In the examples of the present invention, tests were carried out in accordance with the method described below - for measuring adhesive strength and observing the adaptation. The rest results are set out in a table to be given later for better comparison.

MEASUREMENT OF ADHESIVE STRENGTH

After the labial surface of dentin of a bovine foretooth had been polished with emery paper No. 1000, under running water, the water particles deposited was removed from that surface by air-blowing, which was then treated for 60 seconds with the dentin-treating liquid. After the treating liquid had been removed by sufficient water-rinsing, the treated surface to be bonded was dried by air-blowing, and was fixed thereon with a stainless steel column provided on its outside with a threaded groove and having an internal diameter of 4 mm $\phi$ and a height of 2.5 mm by means of a cellophane tape. A small amount of the primer comprising the (meth)acrylic ester polymer in the ethylene related unsaturated monomer containing tri-n-butyl borane was applied by a small brush onto the tooth to be bonded in the column in the form of a single thin layer. Then, after allowing to stand alone at room temperature for 10 minutes, the restorative composite resin was filled and cured in said column. Then, after 20 minutes, the test piece was stored in water at 37° C. for 24 hours. Removed from within the water, the test piece—stainless column +bonded tooth—was fixed respectively on the jig of an Instron universal tester Model 1123. An adhesive force was measured at a tensile rate of 0.5 mm/min, and an adhesion strength was calculated from the bonded area. It is noted that the photopolymerization type restorative composite resin used was OCCLUSIN —trade name—manufactured by ICI, Co., Ltd., and was polymerized by 60-second irradiation with a visible light polymerizer LUXOR manufactured by ICI, Co., Ltd. It is also noted that the chemical polymerization type restorative composite resin used was MICROREST AP —trade name—manufactured by G-C Dental Industrial Corp. and comprising the redox catalyst system of tertiary amine-BPO.

OBSERVATION OF ADAPTATION

A saucer type cavity was formed in the axial surface of a human extracted molar tooth, and the dentin was treated with the dentin-treating liquid and applied with the primer in accordance with the aforesaid method for measuring adhesive strength. The restorative composite resin was filled and cured in the cavity. After curing, the sample was stored in water at 37° C. for 24 hours. Thereafter, the cavity was horizontally cut at its center in the direction normal to the dental axis, and the section was smoothly polished with emery paper No. 1000, under running water. After the section was lightly etched with a solution of phosphoric acid, a precise replica of that section was prepared. The replica's surface was SEM-observed to evaluate the adaptation of the resin to the dentin surface according to the Sasazaki Method for measuring a gap between the resin and the dentin (The Japanese Journal of Conservative Dentistry, Vol. 28, No. 2, pages 452 to 478, 1985). The results are scored in terms of the following five ranks a through e according to that method.

a excellent fit without gap.
b very slight gap.
c gap of 5 $\mu$m or less
d gap of 5 to 10 $\mu$m.
e gap of 10 $\mu$m or more.

The examples of the present invention will now be given below. The results of adhesion strength and evaluation of adaptation are set out in Table 1. It is understood, needless to say, that the present invention is not exclusively limited to such results.

EXAMPLE 1

The dentin-treating liquid used was prepared by adding glutaraldehyde and ferric chloride to a solution containing 0.3 mol/l of EDTA [hereinafter simply called EDTA (0.3M) liquid]in the following proportion, said solution being regulated to a hydrogen ion concentration (pH) of 7.4 with an aqueous solution of sodium hydroxide.

EDTA (0.3M) Liquid: 100 parts by weight
Glutaraldehyde: 3 parts by weight
Ferric Chloride: 1 parts by weight As the ethylene related unsaturated monomer of the primer, use was made of a copolymer consisting of 97 parts by weight of methyl methacrylate and 3 parts by weight of ethylene glycol dimethacrylate, to which a 20.4 weight % or 1 mol/l solution of tri-n-butyl borane in tetrahydrofuran (TBB(1M)THF solution) was added in a weight ratio of 10%. As the polymer of the primer, use was made of a polymer consisting of 20 parts by weight of polymethyl methacrylate (average molecular weight: 800,000 and particle size: 100 Tyler mesh pass) and 80 parts by weight of a copolymer (average molecular weight: 250,000 and particle size: 250 Tyler mesh pass) composed of 40 parts by weight of methyl methacrylate and 60 parts by weight of ethyl methacrylate. The restorative composite resin used was OC- CLUSIN—trade name—of the light polymerization type.

EXAMPLE 2

Dentin-Treating Liquid

EDTA (0.5M) Liquid: 100 parts by weight
Glutaraldehyde: 1 parts by weight
Ferric Chloride: 3 parts by weight

Primer

Ethylene related Unsaturated Monomer: Comonomer of 97 parts by weight of Methyl Methacrylate and 3 parts by weight of Triethylene Glycol Dimethacrylate
Amount of TBB(1M)THF Solution: 10% by weight.
Polymer: Homopolymer of Polymethyl Methacrylate (average molecular weight: 500,000 and particle size: 250 Tyler mesh pass).

Restorative Composite Resin

Chemical Polymerization Type: MICROREST AP - trade name.
These were used for evaluation.

EXAMPLE 3

Dentin-Treating Liquid

EDTA (0.3M) Liquid: 100 parts by weight
Glutaraldehyde: 1 parts by weight
Ferric Chloride: 1 parts by weight

Primer

Ethylene related Unsaturated Monomer:
Commoner of 97 parts by weight of Methyl Methacrylate and 3 parts by weight of Triethylene Glycol Dimethacrylate
Amount of TBB(1M)THF Solution: 10% by weight.
Polymer: Homopolymer of Polymethyl Methacrylate (average molecular weight: 500,000 and particle size: 250 Tyler mesh pass).

Restorative Composite Resin

Light Polymerization Type: OCCLUSIN - trade name.
These were used for evaluation.

EXAMPLE 4

Dentin-Treating Liquid

EDTA (0.5M) Liquid: 100 parts by weight
Glutaraldehyde: 5 parts by weight
Ferric Chloride: 3 parts by weight

Primer

Ethylene related Unsaturated Monomer: Comonomer of 98 parts by weight of Methyl Methacrylate and 2 parts by weight of ethylene Glycol Dimethacrylate
Amount of TBB(1M)THF Solution: 10% by weight.
Polymer: Polymer consisting of 20 parts by weight of Polymethyl Methacrylate (average molecular weight: 800,000 and particle size: 100 Tyler mesh pass) and 80 parts by weight of Copolymer (average molecular weight: 250,000 and particle size : 100 Tyler mesh pass) of 40 parts by weight of methyl methacrylate and 60 parts by weight of ethyl methacrylate.

Restorative Composite Resin

Chemical Polymerization Type: MICROREST AP - trade name.
These were used for evaluation.

EXAMPLE 5

Dentin-Treating Liquid

EDTA (0.3M) Liquid: 100 parts by weight
Glutaraldehyde: 10 parts by weight
Ferric Chloride: 5 parts by weight

Primer

Ethylene related Unsaturated Monomer: Commoner of 98 parts by weight of Methyl Methacrylate and 2 parts by weight of Ethylene Glycol Dimethacrylate
Amount of TBB(1M)THF Solution: 10% by weight.
Polymer: Polymer consisting of 20 parts by weight of Polymethyl Methacrylate (average molecular weight: 800,000 and particle size: 100 Tyler mesh pass) and 80 parts by weight of Copolymer (average molecular weight: 250,000 and particle size : 250 Tyler mesh pass) of 40 parts by weight of methyl methacrylate and 60 parts by weight of ethyl methacrylate.

Restorative Composite Resin

Light Polymerization Type: OCCLUSIN - trade name.
These were used for evaluation.

COMPARATIVE EXAMPLE 1

Dentin-Treating Liquid

EDTA (0.3M) Liquid: 100 parts by weight
Glutaraldehyde: 0 parts by weight
Ferric Chloride: 0 parts by weight

Primer

Ethylene related Unsaturated Monomer: Comonomer of 97 parts by weight of Methyl Methacrylate and 3 parts by weight of Triethylene Glycol Dimethacrylate
Amount of TBB(1M)THF Solution: 10% by weight.
Polymer: Homopolymer of Polymethyl Methacrylate (average molecular weight: 500,000 and particle size: 250 Tyler mesh pass).

Restorative Composite Resin

Light Polymerization Type: OCCLUSIN - trade name.
These were used for evaluation.

COMPARATIVE EXAMPLE 2

Dentin-Treating Liquid

EDTA (0.5M) Liquid: 100 parts by weight
Glutaraldehyde: 0 parts by weight
Ferric Chloride: 3 parts by weight

Primer

Ethylene related Unsaturated Monomer: Comonomer of 98 parts by weight of Methyl Methacrylate and 2 parts by weight of Ethylene Glycol Dimethacrylate
Amount of TBB(1M)THF Solution: 10% by weight.
Polymer: Homopolymer of Polymethyl Methacrylate (average molecular weight: 500,000 and particle size: 250 Tyler mesh pass).

Restorative Composite Resin
Light Polymerization Type: OCCLUSIN - trade name.
These were used for evaluation.

COMPARATIVE EXAMPLE 3

Dentin-Treating Liquid

EDTA (0.5M) Liquid: 100 parts by weight
Glutaraldehyde: 10 parts by weight
Ferric Chloride: 0 parts by weight Primer Ethylene related Unsaturated Monomer: Comonomer of 98 parts by weight of Methyl Methacrylate and 2 parts by weight of Ethylene Glycol Dimethacrylate
Amount of TBB(1M)THF Solution: 10% by weight.
Polymer: Polymer consisting of 20 parts by weight of Polymethyl Methacrylate (average molecular weight: 800,000 and particle size: 100 Tyler mesh pass) and 80 parts by weight of Copolymer (average molecular weight: 250,000 and particle size : 250 Tyler mesh pass) of 40 parts by weight of methyl methacrylate and 60 parts by weight of ethyl methacrylate.

Restorative Composite Resin

Chemical Polymerization Type: MICROREST AP - trade name.
These were used for evaluation.

COMPARATIVE EXAMPLE 4

Dentin-Treating Liquid

Pure Water: 100 parts by weight
Glutaraldehyde: 3 parts by weight
Ferric Chloride: 1 parts by weight Primer Ethylene related Unsaturated Monomer: Comonomer of 98 parts by weight of Methyl Methacrylate and 2 parts by weight of Ethylene Glycol Dimethacrylate
Amount of TBB(1M)THF Solution: 10% by weight.
Polymer: Polymer consisting of 20 parts by weight of Polymethyl Methacrylate (average molecular weight: 800,000 and particle size: 100 Tyler mesh pass) and 80 parts by weight of Copolymer (average molecular weight: 250,000 and particle size : 250 Tyler mesh pass) of 40 parts by weight of methyl methacrylate and 60 parts by weight of ethyl methacrylate.

Restorative Composite Resin

Light Polymerization Type: OCCLUSIN - trade name.
These were used for evaluation.

COMPARATIVE EXAMPLE 5

Dentin-Treating Liquid

EDTA (0.3M) Liquid: 100 parts by weight
Glutaraldehyde: 3 parts by weight
Ferric Chloride: 1 parts by weight Primer Ethylene related Unsaturated Monomer: Comonomer of 97 parts by weight of Methyl Methacrylate and 3 parts by weight of Triethylene Glycol Dimethacrylate
Amount of TBB(1M)THF Solution: 1% by weight.
Polymer: Polymer consisting of 20 parts by weight of Polymethyl Methacrylate (average molecular weight: 800,000 and particle size: 100 Tyler mesh pass) and 80 parts by weight of Copolymer (average molecular weight: 250,000 and particle size : 250 Tyler mesh pass) of 40 parts by weight of methyl methacrylate and 60 parts by weight of ethyl methacrylate.

Restorative Composite Resin

Chemical Polymerizationtype: MICROREST AP - trade name.
These were used for evaluation.

COMPARATIVE EXAMPLE 6

Dentin-Treating Liquid

EDTA (0.5M) Liquid: 100 parts by weight
Glutaraldehyde: 1 parts by weight
Ferric Chloride: 3 parts by weight Primer Ethylene related Unsaturated Monomer: Comonomer of 98 parts by weight of methyl Methacrylate and 2 parts by weight of Ethylene Glycol Dimethacrylate
Amount of TBB(1M)THF Solution: 50% by weight.
Polymer: Polymer consiting of 20 parts by weight of Polymethyl Methacrylate (average molecular weight: 800,000 and particle size: 100 Tyler mesh pass) and 80 parts by weight of Copolymer (average molecular weight: 250,000 and particle size : 250 Tyler mesh pass) of 40 parts by weight of methyl methacrylate and 60 parts by weight of ethyl methacrylate.

Restorative Composite Resin

Light Polymerization Type: OCCLUSIN - trade name.
These were used for evaluation.

TABLE 1

| | | Results of Evaluation | |
| --- | --- | --- | --- |
| | | Adhesion Strength $(kgf/cm^2)$ | Evaluation of Adaptation |
| Example | 1 | 220 | a |
| | 2 | 153 | a |
| | 3 | 212 | a |
| | 4 | 132 | a |
| | 5 | 183 | a |
| Comparative Example | 1 | 19 | e |
| | 2 | 37 | d |
| | 3 | 48 | d |
| | 4 | 8 | e |
| | 5 | 70 | c |
| | 6 | 57 | c |

EFFECT OF THE INVENTION

The dentin-treating liquid containing three essential compounds EDTA, glutaraldehyde and ferric chloride according to the present invention can not only simplify the conventional troublesome method for treating the surface of dentin to be bonded, but also serves to augment collagen of that surface. In view of pulp protection, this liquid is considered to be capable of being used only for the purpose of removing smear layer with high safety. By permitting the primer expected to be grafted to dentinal collagen to be present, it is possible to obtain the adhesive force required for not only the light polymerization type composite resin but also chemical polymerization type composite resin, say, a adhesive force of a minimum of 100 kgf/cm$^2$ and a maximum of 220 kgf/cm$^2$. The observation of the adaptation of the resin to a human extracted tooth have indicated that the bonding of the resin to dentin is so improved that any gap said to be the largest factor of secondary caries it not found at all.

What is claimed is:

1. A method for bonding a composite resin to dentin, which comprises:

treating the surface of dentin with a dentin-treating liquid obtained by adding glutaraldehyde and ferric chloride to an aqueous solution of ethylenediaminetetraacetic acid (abbreviated to EDTA) regulated to a hydrogen ion concentration (pH) of 7.4, removing said treating liquid by water-rinsing to dry the thus treated surface of dentin, applying a primer comprising an ethylene related unsaturated monomer, a (meth)acrylic ester polymer and tri-n-butyl borane on the dried surface of dentin, and filling a restorative composite resin onto the applied surface of dentin.

2. A bonding method as defined in claim 1, wherein the concentration of glutaraldehyde in said treating liquid is 0.01 to 20 parts by weight with respect to 100 parts by weight of water.

3. A bonding method as defined in claim 1 ro 2, wherein the concentration of ferric chloride in said treating liquid is 0.01 to 5.00 parts by weight with respect to 100 parts by weight of water.

4. A bonding method as defined in claim 1 or 2, wherein the concentration of EDTA in said treating liquid is 0.1 to 1.0 mol/l with respect to 100 parts by weight of water.

5. A bonding method as defined in claim 1 or 2, wherein said ethylene related unsaturated monomer of said primer is one or more (meth)acrylic ester monomers.

6. A bonding method as defined in claim 1 or 2, wherein said (meth)acrylic ester polymer of said primer is a methyl methacrylate polymer.

7. A bonding method as defined in claim 1 or 2, wherein said (meth)acrylic ester polymer of said primer is a copolymer of methyl methacrylate and ethyl methacrylate.

8. A bonding method as defined in claim 1 or 2, wherein said (meth)acrylic ester polymer of said primer is a methyl methacrylate polymer and copolymer of methyl methacrylate and ethyl methacrylate.

* * * * *